(12) United States Patent
Lee et al.

(10) Patent No.: US 8,816,836 B2
(45) Date of Patent: Aug. 26, 2014

(54) SAFE OPERATION APPARATUS AND METHOD FOR MOVING OBJECT

(75) Inventors: Byung-Gil Lee, Daejeon (KR); Hyung Kyu Lee, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 143 days.

(21) Appl. No.: 13/305,211

(22) Filed: Nov. 28, 2011

(65) Prior Publication Data

US 2012/0133528 A1 May 31, 2012

(30) Foreign Application Priority Data

Nov. 29, 2010 (KR) ........................ 10-2010-0119915

(51) Int. Cl.
*B60Q 1/00* (2006.01)
(52) U.S. Cl.
USPC ............................ 340/439; 340/575; 340/576
(58) Field of Classification Search
USPC ............................. 340/426.11, 439, 575, 576
See application file for complete search history.

(56) References Cited

U.S. PATENT DOCUMENTS

| 6,060,989 | A  | * | 5/2000 | Gehlot | 340/576 |
| 7,639,148 | B2 | * | 12/2009 | Victor | 340/576 |
| 2006/0191730 | A1 | * | 8/2006 | Alden et al. | 180/272 |
| 2008/0218359 | A1 | * | 9/2008 | Ishida et al. | 340/575 |
| 2012/0069301 | A1 | * | 3/2012 | Hirata | 351/209 |
| 2012/0212353 | A1 | * | 8/2012 | Fung et al. | 340/905 |

FOREIGN PATENT DOCUMENTS

| KR | 10-2002-0034143 | 5/2002 |
| KR | 10-2005-0027814 | 3/2005 |
| KR | 10-2007-0093201 | 9/2007 |

OTHER PUBLICATIONS

Soo-Jin Ahn et al., "Research of the Lane Recognition for an Advanced Vehicle System", Journal of Korean Institute of Information Technology, vol. 5, No. 1, pp. 136-142.

\* cited by examiner

*Primary Examiner* — Brent Swarthout
(74) *Attorney, Agent, or Firm* — Staas & Halsey LLP

(57) ABSTRACT

A safe operation apparatus for a moving object includes: a distraction detection unit for detecting distraction information of a user operating a moving object; a controller for collecting the distraction information from the distraction detection unit, calculating a user's distraction state value, and controlling the moving object to be automatically operated or warning of the distraction state based on the distraction state value; and an automatic operation unit for automatically operating the moving object under the control of the controller. The apparatus further includes a communication unit for transmitting the user's distraction state to a remote control center or an adjacent different moving object under the control of the controller.

14 Claims, 2 Drawing Sheets

SAFE OPERATION APPARATUS AND METHOD FOR MOVING OBJECT

CROSS-REFERENCE(S) TO RELATED APPLICATION

The present invention claims priority of Korean Patent Application No. 10-2010-0119915, filed on Nov. 29, 2010, which is incorporated herein by reference.

FIELD OF THE INVENTION

The present invention relates to a safe operation of an airplane, a ship, a vehicle, or the like, and more particularly, to a safe operation apparatus and method for controlling an operation of a moving object when a user is distracted during running the moving object by measuring a user's distraction by sensing devices, such as an internal optical intelligent camera, a thermal imaging camera or the like, which can sense a distraction of a user running the moving object.

BACKGROUND OF THE INVENTION

In general, in case of vehicles, developed countries such as the united states and the like stipulated laws that prohibit the phone call and the text while driving because of a rapid increase in accidents due to the phone call or the text, but legal systems cannot be a basic solution, and also, domestically, similar distraction accidents in relation to manipulations of devices such as mobile terminals, navigation systems or the like, or watching TV, or the like, are growing rapidly.

Thus, an internal camera recognition system for automatically recognizing and managing a vehicle driver is able to be associated with a real-time automatic operation and warning system upon a driver distraction, as well as prevent a security accident such as vehicle theft, or the like to thus strengthen mutual safety and security, so it may be one of methods capable of preventing risk due to various distractions such as sending a text or making a phone call while driving which are recently on the rise.

Such a distraction causes a serious problem in case of crash between vessels on the sea, and most of accidents on the sea are generally admitted to be caused by carelessness of mates or seamen. However, in actuality, a mate running or operating a vessel cannot concentrate to the operation at every moment, and in most cases, the seamen weary in a state of a full load of fish are away, rather than being in their seat, to sleep through a long period of sailing, and even in an unexpected situation in which vessels crashes suddenly, a remote vessel traffic service (VTS) control center can hardly perform communication, which leads to an accident.

Meanwhile, in case of the possibility of crash of ships, it would be even more effective for a land control center to check motions of every ship to foresee a risky situation and inform a corresponding ship, rather than for the ship itself, to do.

Thus, currently, a sea traffic control system is installed and operated in all of major domestic ports. However, 80% or greater of accidents attributes to the carelessness of seamen, and in case of a severe distraction, even the control center cannot help it.

Also, as for vehicles, recently, the necessity of mounting an indoor camera in a taxi, or the like is increasing, but it merely detects driver's sleepiness. In this case, the method of detecting driver's sleepiness is detecting a motion of the driver's eyelid to determine whether or not he is sleepy. Besides sleepiness, however, recently, the use of a mobile phone or manipulation of vehicle navigation, or the like increasingly causes an accident, and this extends to various distractions from a simple sleepiness to a fatal accident.

That is, in the prior art, a controller keeps his eye on the screen on which ships are displayed using radar, and checks the distance between ships or the like based on his work experience to foresee a crash likelihood between ships and manage the situation, thus performing traffic control. Also, in a ship or airplane, a radar device mounted in the ship or airplane identifies another ship or airplane nearby and refers to it for its sailing or flight.

However, in the prior art, moving object operation method in which the user such as a driver, a mate or the like operating a moving object such as an airplane, a ship, a vehicle, or the like controls the moving object while checking his surroundings directly by his eyes by using the information acquired by radar or the like, when the user's concentration is lowered with, e.g., his sleepiness during driving the moving object, a serious problem may arise in the safety operation.

SUMMARY OF THE INVENTION

In view of the above, the present invention provide a safe operation apparatus and method for controlling an operation of a moving object when a user is distracted during running the moving object by measuring a user's distraction by sensing devices, such as an internal optical intelligent camera, a thermal imaging camera or the like, which can sense a distraction of a user running the moving object.

In accordance with an aspect of the present invention, there is provided a safe operation apparatus for a moving object including: a distraction detection unit for detecting distraction information of a user operating a moving object; a controller for collecting the distraction information from the distraction detection unit, calculating a user's distraction state value, and controlling the moving object to be automatically operated or warning of the distraction state based on the distraction state value; an automatic operation unit for automatically operating the moving object under the control of the controller; and a communication unit for transmitting the user's distraction state to a remote control center or an adjacent different moving object under the control of the controller.

In accordance with another aspect of the present invention, there is provided a safe operation method for a moving object: collecting distraction information on a user who operates a moving object by a distraction detection unit; calculating a user's distraction state value by using the collected distraction information; and controlling an operation of the moving object based on the distraction state value.

BRIEF DESCRIPTION OF THE DRAWINGS

The objects and features of the present invention will become apparent from the following description of embodiments, given in conjunction with the accompanying drawings, in which.

DETAILED DESCRIPTION OF THE EMBODIMENT

Figure 1:
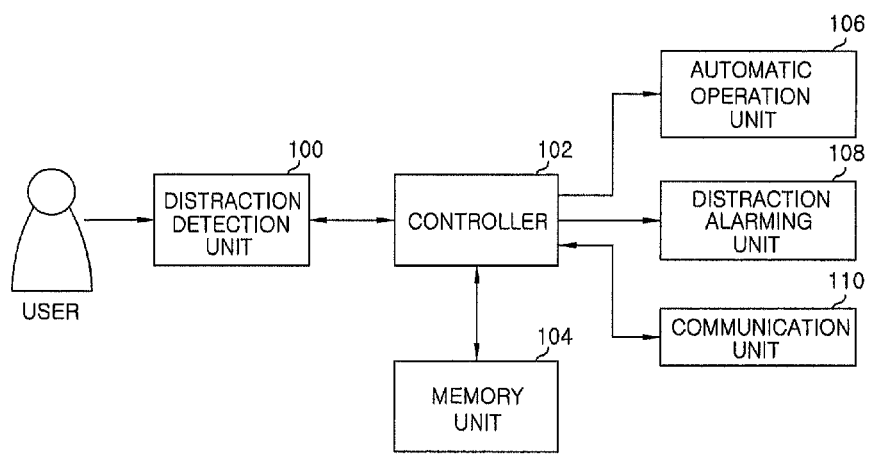
FIG. 1 illustrates a block diagram of a safe operation apparatus for a moving object in accordance with an embodiment of the present invention.

Embodiments of the present invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In the following description of the present invention, if the detailed description of the already known structure and operation may confuse the subject matter of the present invention, the detailed description thereof will be omitted. The following terms are terminologies defined by considering functions in the embodiments of the present invention and may be changed operators intend for the invention and practice. Hence, the terms should be defined throughout the description of the present invention.

Combinations of respective blocks of block diagrams attached herein and respective steps of a sequence diagram attached herein may be carried out by computer program instructions. Since the computer program instructions may be loaded in processors of a general purpose computer, a special purpose computer, or other programmable data processing apparatus, the instructions, carried out by the processor of the computer or other programmable data processing apparatus, create devices for performing functions described in the respective blocks of the block diagrams or in the respective steps of the sequence diagram. Since the computer program instructions, in order to implement functions in specific manner, may be stored in a memory useable or readable by a computer aiming for a computer or other programmable data processing apparatus, the instruction stored in the memory useable or readable by a computer may produce manufacturing items including an instruction device for performing functions described in the respective blocks of the block diagrams and in the respective steps of the sequence diagram. Since the computer program instructions may be loaded in a computer or other programmable data processing apparatus, instructions, a series of processing steps of which is executed in a computer or other programmable data processing apparatus to create processes executed by a computer so as to operate a computer or other programmable data processing apparatus, may provide steps for executing functions described in the respective blocks of the block diagrams and the respective steps of the sequence diagram.

Moreover, the respective blocks or the respective steps may indicate modules, segments, or some of codes including at least one executable instruction for executing a specific logical function(s). In several alternative embodiments, it is noticed that functions described in the blocks or the steps may run out of order. For example, two successive blocks and steps may be substantially executed simultaneously or often in reverse order according to corresponding functions.

Hereinafter, an embodiment of the present invention will be described in detail with the accompanying drawings.

FIG. 1 illustrates a block diagram of a safe operation apparatus for a moving object in a safe way in accordance with the embodiment of the present invention. Operations of respective elements of the safe operation apparatus for a moving object in accordance with the present invention will be described in detail with reference to FIG. 1.

First, a distraction detection unit 100 includes various detection sensors for measuring a user's distraction, such as an intelligent camera, a thermal imaging camera, or a brain wave measuring device or the like. The distraction detection unit 100 is positioned in front of a user who may be a driver, a mate or the like to operate a ship, an airplane, a vehicle and the like to detect eye closing or motion of the user in order to generate user's distraction information.

A controller 102 controls a general operation of the safe operation apparatus depending on an operation program of the safe operation apparatus stored in a memory unit 104. At this time, the controller 102 performs an essential function of recognizing a user, and performs a function of a situation recognition determination system to determine the type and form, structure, feature, situation, degree, and the like of a user's distraction determined depending on the features of a moving object in operation. The situation recognition determination system is very important, and in order to increase reliability based on the user recognition and determination results, various learning results are continuously and additionally stored.

Namely, when the moving object such as an airplane, a ship, a vehicle or the like operates, the controller 102 collects sensing information in relation to the distraction of the user operating the moving object through the distraction detection unit 100. When a distraction degree value of the user calculated through the collected distraction information is included in one of preset reference ranges of multiple stages, it is determined that the user is in a distraction state in which user's concentration required for operating the moving object is lower than a reference, namely, that the user is sleepy or is absent, the controller 102 changes the moving object into an automatic operation mode through a preset method based on the degree of user's distraction or issues an alarm to the user, the remote control center, an adjacent other moving object, or the like.

More specifically, for example, when the controller 102 receives sensing information in relation to the distraction of the user who is operating an airplane, a ship, a vehicle, or the like from the distraction detection unit 100, the controller 102 recognizes the degree of the distraction of the user by using the received sensing information value, and in an instantaneous urgent situation, the controller 102 changes the moving object into an automatic operation mode. In case of a continuous urgent situation because the distraction state continues for more than a certain period of time, the controller 102 directly issues an alarm regarding the distraction state to the corresponding user by making an alarm sound or the like, or provides information about the user's distraction state to the remote control center so that a third party can control the safe operation.

When there is a command for changing of the moving object operated by the user into the automatic operation mode by the controller 102 due to the user's distraction state, an automatic operation unit 106 automatically controls the corresponding moving object based on an automatic operation program preset depending on the characteristics of the moving object such as an airplane, a ship, a vehicle, or the like, irrespective of a user's control.

When the degree value of the user's distraction state corresponds to one of preset reference ranges of multiple stages, a distraction alarming unit 108 issues an alarm directly to the user determined to be in a distraction state by making a voice or an alarm sound through a device such as a speaker, or the like in the moving object under the control of the controller 102.

A communication unit 110 is a device for performing communication with the remote control center or a moving object such as a nearby different ship, airplane, vehicle, or the like. When the degree value of the user's distraction state corresponds to be within a preset certain reference range, the communication unit 110 transmits information regarding the user's distraction state to the remote control center or a moving object such as a nearby different ship, airplane, vehicle, or the like under the control of the controller 102 to guarantee a safe operation of the moving object by a third party.

Figure 2:
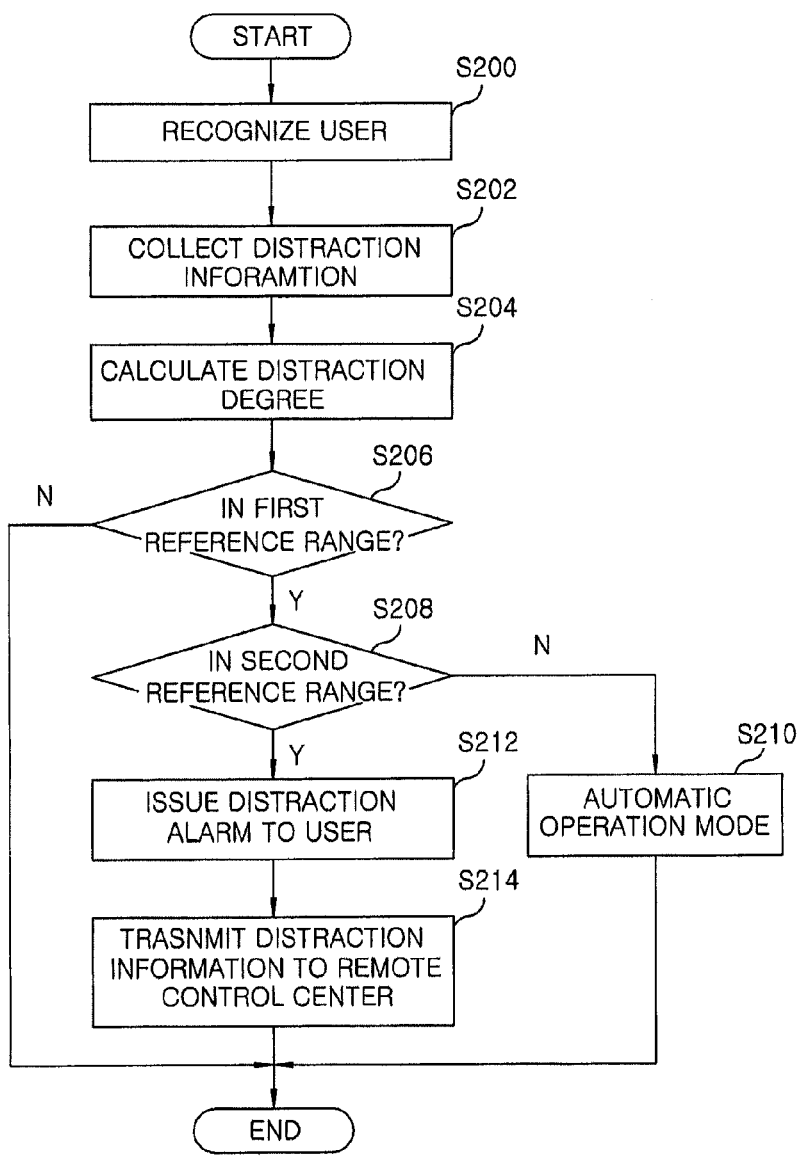
FIG. 2 is a flowchart illustrating a process for controlling a moving object for a safe operation thereof in accordance with the embodiment of the present invention.

FIG. 2 is a flowchart illustrating a process of controlling an operation of a moving object depending on a user's distraction state in a safe operation apparatus for a moving object in accordance with the embodiment of the present invention. The embodiment of the present invention will be described in detail below with reference to FIGS. 1 and 2.

First, the controller 102 recognizes a user who may be a mate, a driver, or the like operating the airplane, ship, or vehicle through an intelligent optical sensor, such as an intelligent camera, or the like, positioned in front of the user provided within the distraction detection unit 100 in step S200.

Next, the controller 102 collects distraction information from various sensors indicating distraction states of users through the distraction detection unit 100 in step S202.

Thereafter, the controller 102 calculates a distraction degree value indicating a user's distraction state such as sleepiness, absence, or the like of the user based on the distraction information regarding the user collected through the distraction detection unit 100 in step S204.

In this case, the distraction degree value refers to a value as a basis for determining user's sleepiness, or the like through comparison with preset reference values. The controller 102 checks whether or not the distraction degree value is within the preset certain reference range to determine a user's distraction state.

Here, for example, the reference range may include a first reference range to determine that the user's distraction state may cause an instantaneous urgent situation in operating the moving object and a second reference range to determine that the user's distraction state may continue for more than a certain period of time to cause a long-term urgent situation in operating the moving object.

Here, for example, the first reference range may be made by combining following information: 1) a time when a motion of a face is detected to be toward a mobile phone (or hand) while driving, rather than a motion of the face keeping eyes forward, 2) a time period during which a motion of pupils of the eyes not kept forward is continuously detected while driving, 3) a time period during which a mobile phone (or hand) positioned near user's ear is continuously detected while driving, 4) a delay in time (speed) of blinking eyes, and 5) a reduction in an overall opening rate of eyes.

Also, for example, the second reference range may be made by combining following information: 1) detection of a motion of a face to be toward a mobile phone (or hand) is detected, rather than a motion of a face keeping eyes forward, by exceeding a certain period of time while driving, 2) detection of a motion of pupils of the eyes not kept forward by exceeding a certain period of time while driving, 3) detection of a mobile phone (or hand) positioned near user's ear by exceeding a certain period of time while driving, 4) detection of sleep by a thermal imaging camera or a brain wave measuring device, 5) detection of a delay in time (speed) of blinking eyes by exceeding a certain period of time, and 6) detection of reduction in an overall opening size of eyes by exceeding a certain rate in a normal state.

Namely, the controller 102 checks whether or not the distraction state value is included in the first reference range in step S206, and then continuously checks whether or not it is included in the second reference range in step S208.

When the distraction degree value is included in the first reference range in which a particular distraction state of the user can be determined, the controller 102 determines that the user's distraction state will cause an instantaneous urgent situation of the moving object, like a short sleepiness, or the like, and controls the automatic operation unit 106 to change the moving object into an automatic operation mode, thus resolving the urgent situation in step S210.

Meanwhile, when the distraction degree value is included in the second reference range in which a particular continuous distraction state of the user can be determined, the controller 102 determines that the user's distraction state will cause a continuous urgent situation of the moving object, like a deep sleep, absence, or the like, and controls the distraction alarming unit 108 to issue an alarm regarding the user's distraction state through a sound or an alarm sound using a speaker, or the like installed in the moving object in step S212.

Further, when the controller 102 determines that the user's distraction state will cause a continuous urgent situation of the moving object, like a deep sleep, absence, or the like, the controller 102 may transmit information regarding the user's distraction state to a remote control center or an adjacent different moving object through the communication unit 110 to guarantee a safe operation of the moving object by a third party, besides the direct alarming method through the distraction alarming unit 108.

As described above, in the safe operation apparatus and method for controlling an operation of a moving object, such as airplane, a ship, a vehicle, or the like, a user's distraction is measured by using sensing devices, such as an internal optical intelligent camera, a thermal imaging camera or the like, which can sense a distraction of a user who runs an airplane, a ship, a vehicle, or the like, and the degree of the user's distraction is recognized based on the measured distraction information, whereby, in an instantaneous urgent situation, the moving object is changed into an automatic operation mode, or when a distraction state is maintained for more than a certain period of time, the user is warned of or information regarding the corresponding situation is provided to a remote control center, or the like, thus ensuring a safe operation of the moving object.

While the invention has been shown and described with respect to the preferred embodiments, it will be understood by those skilled in the art that various changes and modifications may be made without departing from the scope of the invention as defined in the following claims.

What is claimed is:

1. A safe operation apparatus of a moving object comprising:
   a distraction detection unit to detect distraction information including measured state of a user in operating a moving object;
   a controller to calculate a degree of a user's distraction state value when determining the distraction information is included in reference ranges, and control the moving object to be automatically operated when the degree of the user's distraction state value is within a first of the reference ranges, and issue warning when the degree of the user's distraction state value is outside the first of the reference ranges and within a second of the reference ranges;
   an automatic operation unit to automatically operate the moving object under the control of the controller; and a communication unit to transmit the degree of the user's distraction state to a remote control center or an adjacent different moving object under the control of the controller, wherein when the distraction state value is included in the first of the reference ranges indicating an instantaneous urgent situation, the controller changes an operation mode of the moving object into an automatic operation mode, wherein when the distraction state value is included in the second of the reference ranges indicating a continuous urgent situation, the controller issues an alarm to reveal the user's distraction state to the user, and wherein when the distraction state value is included in the second of the reference ranges indicating a continuous urgent situation, the controller transmits the user's distraction state to a remote control center.

2. The apparatus of claim 1, wherein the controller issues an alarm as a voice or warning sound regarding the user's distraction state through a speaker provided in the moving object.

3. The apparatus of claim 1, wherein when the distraction state value is included in the second of the reference ranges indicating a continuous urgent situation, the controller transmits the user's distraction state to a different moving object within a preset adjacent area.

4. The apparatus of claim 1, wherein the distraction detection unit includes sensors of an intelligent camera, thermal imaging camera and a brain wave measuring device for detecting motion or sleepiness of user.

5. The apparatus of claim 1, wherein the distraction detection unit includes an intelligent camera installed in front of the user for detecting a user's motion.

6. The apparatus of claim 1, wherein the mobile object includes at least one of an airplane, a ship, and a vehicle.

7. A safe operation method of a moving object comprising:
 detecting distraction information including measured state of a user who operates a moving object by a distraction detection unit;
 calculating a degree of a user's distraction state value when determining the distraction information is included in reference ranges; and
 controlling an operation of the moving object based on the degree of user's distraction state value, and
 wherein the controlling causes the moving object to be automatically operated when the degree of the user's distraction state value is within a first of the reference ranges, and issues warning when the degree of the user's distraction state value is outside the first of the reference ranges and within a second of the reference ranges, wherein, in said controlling an operation of the moving object, when the distraction state value is included in the first of the reference ranges indicating an instantaneous urgent situation, an operation mode of the moving object is changed into an automatic operation mode, wherein, in said controlling an operation of the moving object, when the distraction state value is included in the second of the reference ranges indicating a continuous urgent situation, an alarm is issued to reveal the user's distraction state to the user, and wherein, in said controlling an operation of the moving object, when the distraction state value is included in the second of the reference ranges indicating a continuous urgent situation, the user's distraction state is transmitted to a remote control center.

8. The method of claim 7, wherein an alarm is issued as a voice or warning sound through a speaker provided in the moving object.

9. The method of claim 7, wherein, in said controlling an operation of the moving object, when the distraction state value is included in the second of the reference ranges indicating a continuous urgent situation, the user's distraction state is transmitted to a different moving object within a preset adjacent area.

10. The method of claim 7, wherein the distraction detection unit includes sensors of an intelligent camera, thermal imaging camera and a brain wave measuring device for detecting motion or sleepiness of user.

11. The method of claim 7, wherein the distraction
 detection unit includes an intelligent camera installed in front of the user for detecting a user's motion.

12. The method of claim 7, wherein the distraction detection unit includes a thermal imaging camera installed in front of the user for detecting the driver's motion.

13. The method of claim 7, wherein the mobile object includes at least one of an airplane, a ship, and a vehicle.

14. The apparatus of claim 1, wherein the first of the reference ranges and the second of the reference ranges combine different items of the distraction information collected via the detection unit.

\* \* \* \* \*